US00PP29940P2

(12) United States Plant Patent
Hansen

(10) Patent No.: US PP29,940 P2
(45) Date of Patent: Dec. 4, 2018

(54) ***LAGERSTROEMIA* PLANT NAMED 'COOL BEANS'**

(50) Latin Name: ***Lagerstroemia* (L.) hybrid**
Varietal Denomination: Cool Beans

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 15/732,697

(22) Filed: Dec. 15, 2017

(51) Int. Cl.
*A01H 5/00* (2018.01)

(52) U.S. Cl.
USPC ..... Plt./252

(58) Field of Classification Search
USPC ..... Plt./252
See application file for complete search history.

*Primary Examiner* — Annette H Para

(57) ABSTRACT

The new and distinct crape myrtle plant named *Lagerstroemia* 'Cool Beans' has a dense, short, compact, broadly rounded habit, is ground hardy to at least USDA zone 6, has deep green foliage edged in rosy red. The flowers arise from shiny, rosy-red buds, are lightly fragrant, large, cover the shrub with their pinkish color. The new plant resists leaf spot and powdery mildew and is useful in the landscape as a specimen, en masse, or as a container plant.

1 Drawing Sheet

Botanical classification: *Lagerstroemia* (L.) hybrid.
Variety denomination: 'Cool Beans'.

BACKGROUND OF THE INVENTION

The present invention relates to a new and distinct cultivar of *Lagerstroemia* plant, commonly known as crape myrtle, and hereinafter referred to by the cultivar name 'Cool Beans' or the "new plant." 'Cool Beans' is grown primarily as an ornamental for landscape use and for use as a potted plant and is the result of an ongoing breeding program to produce new and improved garden worthy plants for the ornamental market. The new plant was the result of pollination in an isolation block in August of 2012 at a wholesale perennial nursery in Zeeland, Mich., USA using the unreleased proprietary hybrid H10-11-02 (not patented) as the seed or female parent and a sibling of H10-11-02 as the male or pollen parent (not patented). The new plant was given the breeder code 12-28-6.

No plants of *Lagerstroemia* 'Cool Beans' have been sold, in this country or anywhere in the world, prior to the filing of this application, nor has any disclosure of the new plant been made prior to the filing of this application with the exception of that which may have been disclosed or sold within one year of the filing of this application and was either derived directly or indirectly from the inventor.

*Lagerstroemia* 'Cool Beans' was initially asexually propagated by stem cuttings at a wholesale perennial nursery in Zeeland, Mich., USA in 2014. The resultant plants from successive generations have demonstrated that the new plant has remained stable and true to type in multiple and successive generations of asexual propagation.

SUMMARY OF THE INVENTION

Plants of the new cultivar 'Cool Beans' have not been observed under all possible environmental conditions. The phenotype may vary somewhat with changes in light, temperature, soil and available moisture and fertility without, however, any variance in genotype.

The following traits have been repeatedly observed and are determined to be unique characteristics of 'Cool Beans'. Among the characteristics in combination which distinguish 'Cool Beans' as a new and distinct cultivar, unique from all other cultivars known to the inventor are:

1. Dense, short, compact, broad, rounded growth habit;
2. Semi-glossy foliage of deep olive green edged with rosy red;
3. Heavily-branched rosy reddish-colored stems;
4. Pinkish flowers open from rosy red buds on new growth to cover the shrub;
5. Resistance to Cercospora leaf spot and Erisphe powdery mildew;
6. Ground hardy to at least USDA hardiness zone 6.

'Cool Beans' is distinguished from its female parent with flowers that are cool-pinkish colored and a more compact rounded habit. The most similar cultivars known to the inventor include: 'Spiced Plum' U.S. Plant patent application Ser. No. 15/530,535, 'Sweet Macchiato' U.S. Plant Pat. No. 28,759, 'Whitt VI' U.S. Plant Pat. No. 14,438 and 'Catawba' (not patented). 'Catawba' is much taller in habit and has flowers of more purple. 'Spiced Plum' has a smaller habit and the flowers are deeper raspberry-purple with no reddish margins of the foliage. 'Sweet Macchiato' has flowers that are paler pink and the foliage has a deeper and more intense burgundy tinting. 'Whitt VI' is much larger in habit and has flowers of more white than the new plant. Compared with 'Bubble Tea' U.S. Plant Patent, the new plant is similar in habit, but the flower color of the new plant is more pink and less lavender. Compared with the female parent the new plant is slightly taller and the flower color is deeper pink with less lavender.

BRIEF DESCRIPTION OF THE DRAWINGS

The accompanying color photographs illustrate the flower and foliage characteristics and the overall appearance of 'Cool Beans', showing the colors as true as it is reasonably possible to obtain in color reproductions of this type. Colors in the photographs may differ slightly from the color values cited in the detailed botanical description which accurately describe the colors of the new *Lagerstroemia*.

DETAILED BOTANICAL DESCRIPTION

Figure 1:
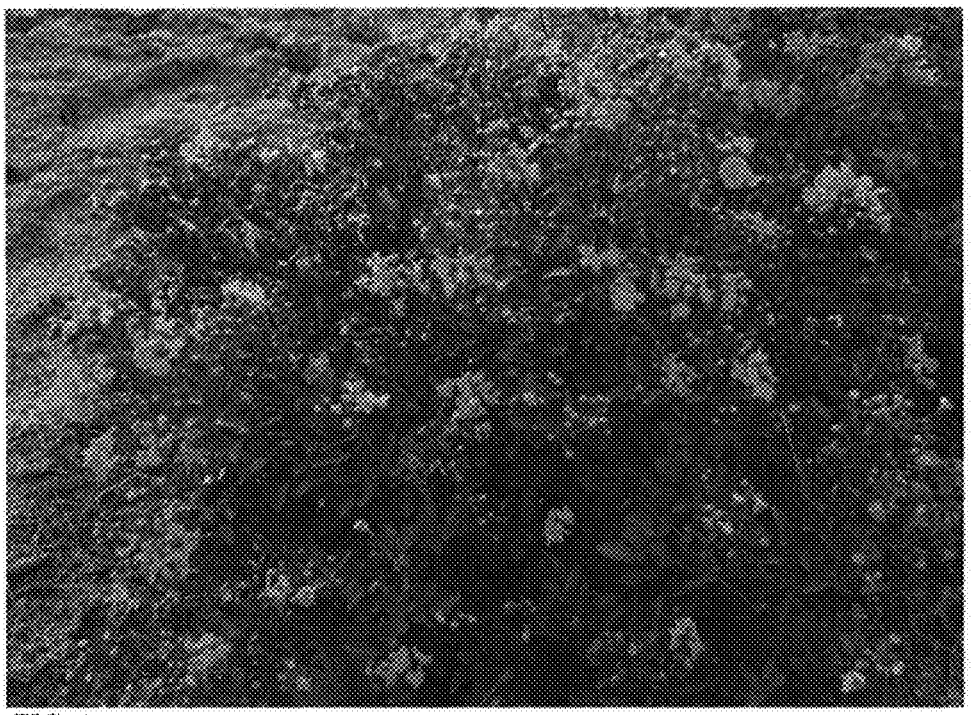
FIG. 1 shows a three-year-old plant in a trial area in late summer peak flowering.
Figure 2:
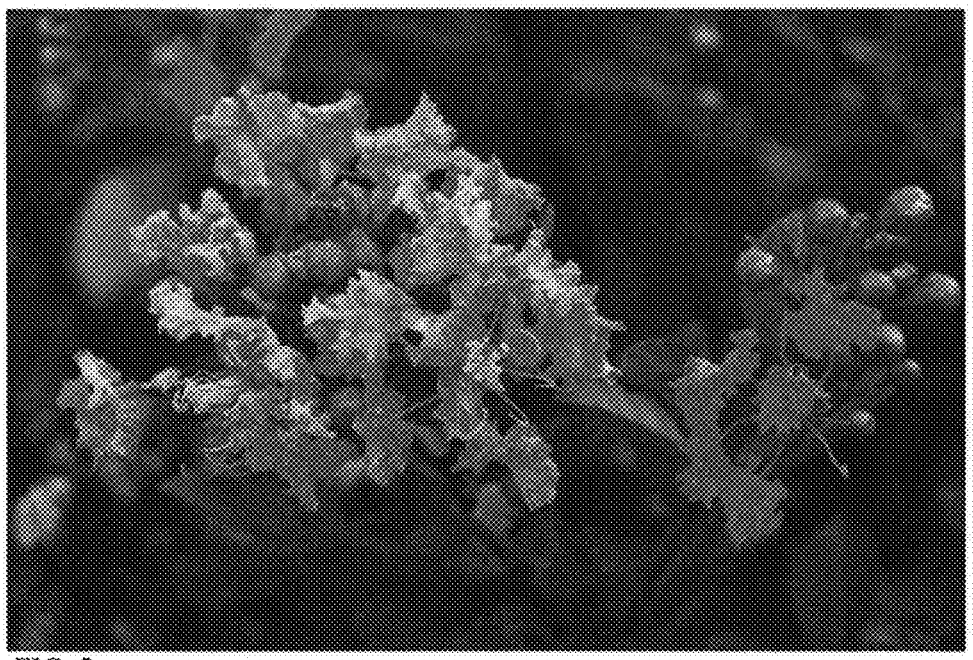
FIG. 2 shows a close-up for the flowers and buds.

The following color references are based on the 2015 edition of The Royal Horticultural Society Colour Chart except where common dictionary terms are used. The following observations and size descriptions are of approximately five-year-old plants grown in a loamy-sand, full-sun, open trial bed in Zeeland, Mich., USA with supplemental water and fertilizer as needed. The phenotype may vary slightly with different environmental conditions, such as temperature, light, fertility, moisture and maturity levels, but without any change in the genotype.

Botanical classification: *Lagerstroemia* L.;

Parentage: Female, or seed parent H10-11-02; the male, or pollen parent is sibling to H10-11-02;

Propagation: Terminal softwood stem cuttings;

Time to initiate roots: About three weeks;

Growth rate: Moderate; finishing from a 65 mm liner in a 3.7 liter container in about 10 weeks;

Plant description: Deciduous, woody, narrow, compact flowering shrub; about six mainly upright to outward primary stems; freely branched;

Root description: Fine, numerous, fibrous, well-branched;

Plant habit: About 74 cm high from the soil level to the top of the inflorescences; about 86 cm wide with no pinching, pruning or plant growth regulators;

Stems: To about 74.0 cm long and about 10.0 mm diameter at base, terete; young stems terete with four longitudinal carinae, along line on either side of petioles; highly branched with about 10 to 14 alternate branches held at about 60 degree angle above horizontal; branches to about 25 cm long and 3.5 mm diameter at base;

Stem color: Woody basal 15 cm of blend between RHS 164C and RHS 165C with exfoliating striations of nearest RHS 165B; young developing stems striated with nearest RHS 181B and a blend between RHS 191B and RHS 181C;

Node: About 20 to 25 per main stem; internode length average about 2.2 cm in main stems;

Node color: Same as surrounding stem;

Foliage description: Sub-opposite to alternate; simple; ovate; margin ciliolate, slightly involute; acute apex; rounded to attenuate base; to about 5.0 cm long and 2.6 cm wide, average about 4.5 cm long and 2.4 cm wide; adaxial and abaxial glabrous and lustrous;

Abaxial leaf color: Young emerging leaf adaxial nearest RHS 137B with blush of nearest RHS 187A and 1.0 mm margin nearest RHS 187A, abaxial nearest RHS 147B with light blush of nearest RHS 187A; mature leaf adaxial nearest RHS 137A and 1.0 mm margin nearest RHS 187A, abaxial between RHS 148A and RHS 148B lightly blushed with RHS 187A;

Veins: Pinnate, puberulent adaxial and abaxial;

Vein color: Young emerging leaf adaxial midrib base nearest RHS 146D, abaxial nearest RHS 160C with faint blush of RHS 187A; mature adaxial veins nearest RHS 147C faintly blushed with nearest RHS 187A; mature abaxial veins between RHS 147C and RHS 137B;

Petiole: Sessile;

Inflorescence: Panicle; terminal branched panicles up to about 480 flowers; average about 320 flowers; up to about 55.0 cm long and about 25.0 cm across; beginning late-summer and continuing until fall, for about eight weeks;

Buds: Globose to ellipsoidal with rounded to slightly cuspidate apex and rounded base; laevigate; glabrous; about 8.0 mm long and about 7.0 mm diameter one day prior to opening;

Bud color: Exposed petals nearest RHS 73C; proximal one-half of calyx blend between RHS 152D and RHS 146D with blush of nearest RHS 183A, distal one-half of calyx between RHS 178C and RHS 179B with carina between RHS 178A and RHS 177A;

Flowers: Perfect; regular; actinomorphic; terminal panicle; individually about 2.5 cm across and about 22.0 mm long to tip of style, corolla to about 16.0 mm long; lasting about two days;

Flower fragrance: Lightly sweet;

Peduncle: Terete with four longitudinal carinae in proximal portion and terete in distal portion; about 6.0 mm diameter at base below lowest flowering branch, to about 55.0 cm long;

Peduncle color: Variable with position; proximal blend between RHS 164C and RHS 165C and distal portion blend between RHS 164C and RHS 165C.

Pedicel: Terete; glabrous; nitid; about 6.0 mm long and 1.0 mm diameter;

Pedicel color: Nearest RHS N186C;

Sepals: Fused in about the basal 4.0 mm; acute apex, entire margin; glabrous and laevigate both adaxial and abaxial; about 8.0 mm long and individually about 4.0 mm long above the fusion and about 3.0 mm wide at fusion point;

Sepal color: Adaxial basal 5.0 mm lighter than RHS 145D, distal 3.0 mm nearest RHS 183B; abaxial basal 5.0 mm nearest RHS 184B, distally nearest RHS 183A; adaxial basal 5.5 mm nearest RHS 150D, portion below apex nearest RHS 184B and apex between RHS 194C and RHS 194D; abaxial basal 5.5 mm nearest RHS 145B, portion below apex nearest RHS 183B and apex nearest RHS 181B;

Petals: Six; stalked; glabrous; blade ruffled or crisped; margin crisped; blade with rounded apex and cordate to sagittate base, to about 12.0 mm across and 17.0 mm long; claw base adnate to calyx, to about 7.0 mm long and 0.5 mm diameter; overall about 1.8 cm long; blade to about 10.0 mm long and about 12.0 mm across;

Petal color: Blade adaxial and abaxial blend between RHS 61C and RHS 63B; claw nearest RHS 61B;

Androecium:

*Stamens*.—Typically about 36; six longer and about 30 shorter;

*Filaments*.—Shorter stamens to about 10.0 mm long and about 0.2 mm diameter, curved to twisted; longer filaments about 17.0 mm long and about 0.5 mm diameter; color of shorter filaments translucent to nearest RHS NN155B; color longer filaments proximal two-thirds nearest RHS 53C, distal one-third nearest RHS 150D;

*Anthers*.—Flattened ellipsoid; more developed on longer stamens to about 1.2 mm long and 1.0 mm across, on shorter stamens about 1.0 mm long and about 0.7 mm across; color nearest RHS 13B;

*Pollen*.—Abundant on longer stamens; color nearest RHS 14B;

Gynoecium: One;

*Style*.—Terete; glabrous; about 22.0 mm long and 0.8 mm diameter; color nearest RHS 53B in the middle portion, distally nearest RHS 53A and base nearest RHS 53B;

*Stigma*.—Globose; about 1.0 mm diameter; color nearest RHS 138B;

*Ovary*.—Superior; ellipsoidal; about 3.0 mm tall and 2.0 mm diameter; color between RHS 150D and RHS 145D;

Fruit: No seeds observed in Zeeland, Mich.;

Seed: No seeds observed in Zeeland, Mich.;

Disease resistance: *Lagerstroemia* 'Cool Beans' has shown resistance to powdery mildew and black leaf spot, Erisphe and Cercospora fungi, respectively. Other resistance beyond that typical for crape myrtle has not been observed. The new plant's root system is capable of withstanding cold temperatures typical of those found in USDA zone 6.

It is claimed:

1. A new and distinct cultivar of crape myrtle plant named *Lagerstroemia* 'Cool Beans' essentially as herein illustrated and described.

* * * * *